United States Patent
Chu et al.

(10) Patent No.: US 9,823,213 B2
(45) Date of Patent: Nov. 21, 2017

(54) ELECTROCHEMICAL TEST STRIP, MEASUREMENT SYSTEM AND METHOD FOR DETERMINING SAMPLE CONTENT IN THE REACTIVE REGION OF THE ELECTROCHEMICAL TEST STRIP

(71) Applicant: Apex Biotechnology Corp., Hsinchu (TW)

(72) Inventors: Ching Yuan Chu, Hsinchu (TW); Chun Ming Cheng, Hsinchu (TW); Po Min Wang, Hsinchu (TW); Lee Teng Yi Wu, Hsinchu (TW)

(73) Assignee: Apex Biotechnology Corp., Hsinchu (TW)

( * ) Notice: Subject to any disclaimer, the term of this patent is extended or adjusted under 35 U.S.C. 154(b) by 56 days.

(21) Appl. No.: 14/832,883

(22) Filed: Aug. 21, 2015

(65) Prior Publication Data

US 2016/0131610 A1 May 12, 2016

(30) Foreign Application Priority Data

Nov. 10, 2014 (TW) .............................. 103138891 A (51) Int. Cl.
*G01N 27/327* (2006.01)

(52) U.S. Cl.
CPC ..... *G01N 27/3272* (2013.01); *G01N 27/3274* (2013.01)

(58) Field of Classification Search
CPC ............. G01N 27/327; G01N 27/3271; G01N 27/3272; G01N 27/3274
See application file for complete search history.

(56) References Cited

U.S. PATENT DOCUMENTS

| 5,264,103 A * | 11/1993 | Yoshioka ............... C12Q 1/004 204/403.1 |
| 5,266,179 A * | 11/1993 | Nankai ............ G01N 33/48771 204/401 |
| 5,582,697 A | 12/1996 | Ikeda et al. |
| 6,743,635 B2 | 6/2004 | Neel et al. |
| 7,452,457 B2 | 11/2008 | Burke et al. |

(Continued)

FOREIGN PATENT DOCUMENTS

| TW | 201202705 A1 | 1/2012 |
| TW | I388823 B1 | 3/2013 |
| TW | 201520545 A | 6/2015 |

OTHER PUBLICATIONS

TIPO; Search Report dated Nov. 10, 2015 in Taiwanese Application No. 103138891.

(Continued)

*Primary Examiner* — Alexander Noguerola
(74) *Attorney, Agent, or Firm* — Snell & Wilmer L.L.P.

(57) ABSTRACT

An electrochemical test strip, measurement system and method for determining sample content in the reactive region of the electrochemical test strip are presented. The electrochemical test strip comprises an insulator substrate which includes an electrode system disposed thereon. The electrode system includes at least one pair of electrodes. A lower plate which includes a reactive region and a sampling cell is disposed on the insulator substrate. An upper plate is disposed on the lower plate, wherein the at least one pair of electrodes is designed as an electrical loop adjacent to the sampling port.

3 Claims, 9 Drawing Sheets

(56) References Cited

U.S. PATENT DOCUMENTS

2004/0182703 A1* 9/2004 Bell .................. C12Q 1/006
 204/403.11
2012/0061259 A1* 3/2012 Lin .................. C12Q 1/005
 205/792

OTHER PUBLICATIONS

TIPO; Office Action dated Nov. 17, 2015 in Taiwanese Application No. 103138891.

* cited by examiner

ELECTROCHEMICAL TEST STRIP, MEASUREMENT SYSTEM AND METHOD FOR DETERMINING SAMPLE CONTENT IN THE REACTIVE REGION OF THE ELECTROCHEMICAL TEST STRIP

CROSS REFERENCE TO RELATED APPLICATIONS

This application claims the right of priority based on Taiwanese Patent Application No. 103138891 entitled "ELECTROCHEMICAL TEST STRIP, MEASUREMENT SYSTEM AND METHOD FOR DETERMINING SAMPLE CONTENT IN THE REACTIVE REGION OF THE ELECTROCHEMICAL TEST STRIP," filed on Nov. 10, 2014, which is incorporated herein by reference and assigned to the same assignee herein.

FIELD OF THE INVENTION

The present invention relates to an electrochemical test strip and a measurement system therefor, and more particularly to an electrochemical test strip with electrode set taken a circuit design near sampling port of the strip, a measurement system, and method for determining sample volume in reaction region of the electrochemical test strip.

BACKGROUND OF THE INVENTION

With advances in medicine and conceptual increments of modern medical care, more and more attentions have been paid to fast, inexpensive, small-volume, and self-test product which does not require for professionals to operate (such as blood glucose meters, electronic ear thermometers, and electronic sphygmomanometers, etc.). In both medical and biochemical assays, using an electrochemical test strip has already been a common technique. Conventional electrochemical test strips includes at least two measuring electrodes. After the sample is injected into the reaction region of the test strip, characteristics of the sample can be measured by at least two measuring electrodes. Under such construction, however, whether the sample has been completely covered the measuring electrode is unable to be determined prior to operating measurements. Moreover, whether the sample is injected and entered into the reaction zone is unable to be ensured.

With reference to currently background art, there are a variety of technical solutions existed to solve the background problems. For example, U.S. Pat. No. 5,582,697, the entity of which is incorporated herein by reference, discloses an electrochemical test strip with three electrodes. A third electrode is introduced in the reaction region and placed the most distant from the entrance of the reaction zone compared to the other two measuring electrodes. After injection of the sample, by detecting the current change of the two measuring electrodes between the closest to the inlet and the farthest from the entrance in the reaction region to determine whether the sample properly covers these measuring electrodes. Another U.S. Pat. No. 6,743,635 discloses an electrochemical test strip with four electrodes. In addition to the first and second electrodes, a third and a fourth electrodes are introduced in the reaction region and placed the most distant from the entrance of the reaction zone compared to the other two measuring electrodes. After the sample is injected into the reaction region by capillarity, the third and fourth electrodes are electrically connected by using the capacity of conductivity of liquid samples, thereby confirming that the sample covers the measuring electrodes. The methods to determine the status of sample discloses in U.S. Pat. Nos. 5,582,697 and 6,743,635, however, cannot accurately detect whether the sample fully covers measuring electrodes. For example, referring FIGS. 4A-4E, when an insufficient amount of sample enters into a reaction region of an electrochemical test strip, the sample partially covers the ends of the measuring electrodes due to a hydrophilic structure of electrochemical test strip and capillary action. The third electrode of U.S. Pat. No. 5,582,697 and the third and fourth electrodes of U.S. Pat. No. 6,743,635 still can be electrically conducted, enforcing the detection equipment to perform concentration detection. However, the sample volume is insufficient, resulting in incomplete chemical reactions on the measuring electrodes, severely under-estimated measurement data, and erroneous measurement results.

As to other related background art, Taiwanese Patent No. 1388823 discloses a third electrode added in the reaction region. The third electrode is placed the most distant from the entrance of the reaction zone compared to the other two measuring electrodes. With this third electrode in operated with measuring electrodes, capacitance value of the sample can be measured, and the sample volume can also be determined. In addition, U.S. Pat. No. 7,452,457 discloses an electrochemical test strip with at least three electrodes. A third electrode is placed the most distant from the entrance of the reaction zone compared to the other two measuring electrodes. With the use of AC signal to measure the reaction amplitude or phase angle of the test sample, the sample volume can therefore be calculated. During the process for detecting the electrochemical concentration, the sample contains many substances with electrical reaction signals. For example, during the process of blood measurement, hematocrit volume will seriously affect the measured capacitance value. The concentrations of glucose and uric acid affecting on the magnitudes of reaction signals will cause inaccurate determination for measurement systems disclosed in Taiwanese Patent No. 1388823 and U.S. Pat. No. 7,452,457. This is attributed to only considering by reference with a single reaction signal, resulting in ineffective determination of insufficient sample volume as shown in FIGS. 4A-4E and failure judgement of the measuring system.

Further, each of the abovementioned background art requires at least one dedicated electrode additionally set in a place the most distant from the entrance of the reaction region to proceed with measurement for the sample volume, resulting in volume increment of test strip and sampling. Accordingly, an electrochemical test strip configured to correctly identify the sample volume and with reduced number of electrodes is needed for the industry.

SUMMARY OF THE INVENTION

Aspects of the present invention provide an electrochemical test strip with electrode set taken a circuit design near sampling port of the strip, a measurement system, and method for determining sample volume in reaction region of the electrochemical test strip. The sample volume in the reaction region can be determined by using the electrode loop design adjacent to the sampling port and analyzing the difference of volume signals.

According to some embodiments of the invention, an electrochemical test strip comprises: an insulator substrate with an electrode system disposed thereon, the electrode system comprising at least one first set of electrodes and second set of electrodes; a lower separated plate disposed on the insulator substrate and including a reactive region and a port for sampling; a reactive layer placed on the reaction region; and an upper separated plate disposed above the lower plate, wherein the first set of electrodes is designed for a first signal loop for sample volume and the second set of electrodes is designed for a second signal loop for sample volume characterized in that the first and second signal loops reflect on a volume of the reaction region.

According to other embodiments of the invention, an electrochemical measurement system comprises: the electrochemical test strip; a connector transmitting a corresponding reaction signal generated from the sample on the electrochemical test strip to the electrochemical measurement system, a calculation unit configured to convert reaction signals on the electrochemical test strip; a digital converter configured to transform the corresponding reaction signal to a digital reaction signal; and a signal processor processing the digital reaction signal and showing a corresponding result on a display.

According to other embodiments of the invention, a method for determining a sample volume in a reaction region of an electrochemical test strip comprises: providing an electrochemical test strip; placing the electrochemical test strip into the electrochemical measurement system; providing a signal to the first and second sets of electrode of the electrochemical test strip; performing measurement of a first volume signal and a second volume signal using the electrochemical measurement system; analyzing and determining a sample volume in the reaction region based on a signal difference using the signal processor, if the sample volume is sufficient, then proceeding with a concentrating measurement step; if the sample volume is deficient, then demanding redo measurement or adding more sample to the reaction region.

BRIEF DESCRIPTION OF THE PICTURES

The foregoing aspects and many of the attendant advantages of this invention will become more readily appreciated by reference to the following detailed description, when taken in conjunction with the accompanying pictures, wherein.

DETAILED DESCRIPTION OF THE INVENTION

Reference will now be made in detail to several exemplary embodiments of the invention, examples of which are illustrated in the accompanying drawings. Wherever possible, the same reference numbers are used in the drawings and the description to refer to the same or like parts. In the drawings, the shape and thickness of an embodiment may be exaggerated for clarity and convenience. Note that the features illustrated in the drawings are not necessarily drawn to scale. Descriptions of well-known components, materials, and process techniques may be omitted so as to not unnecessarily obscure the embodiments of the invention. Any devices, components, materials, and steps described in the embodiments are only for illustration and not intended to limit the scope of the present invention.

Figure 1:
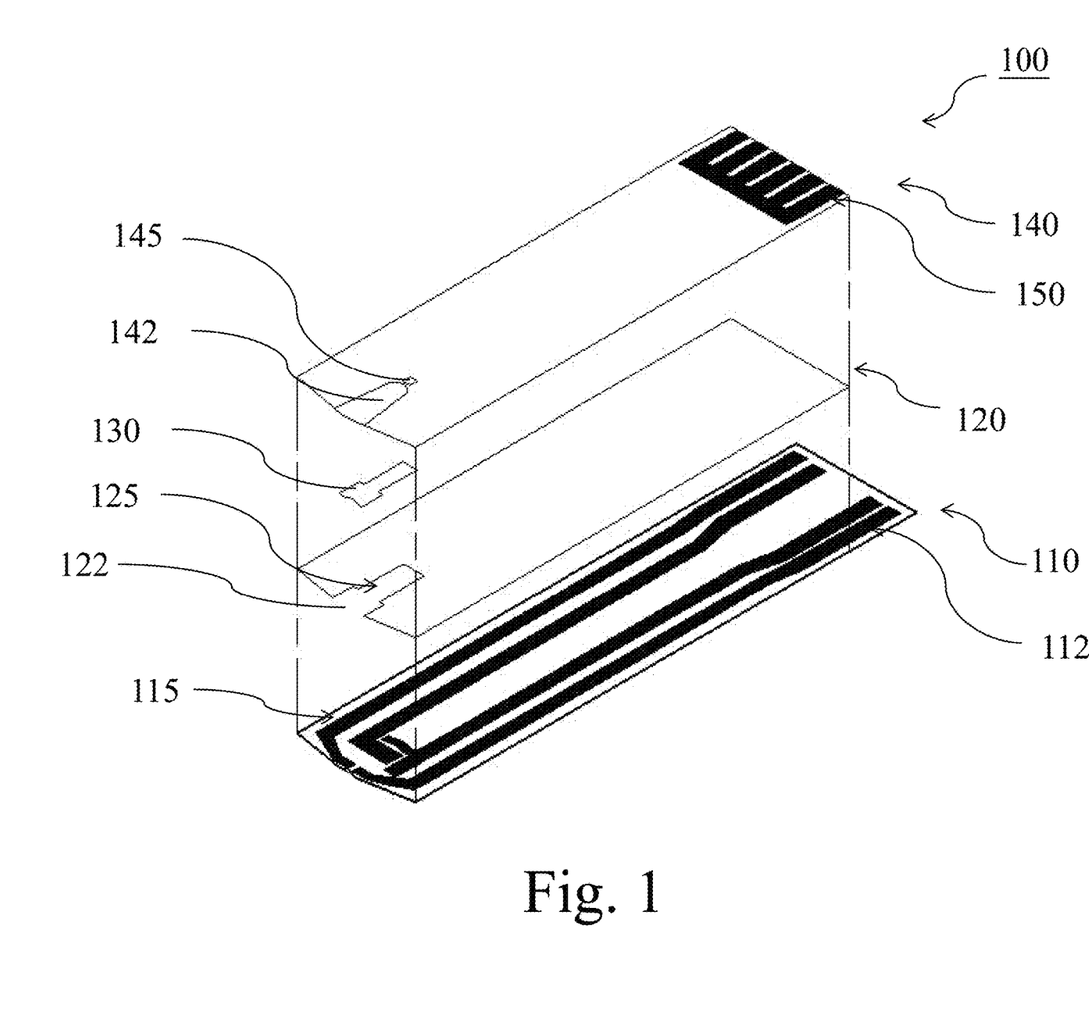
FIG. 1 is an exploded view schematically illustrating the structure of the electrochemical test strip according to an embodiment of the invention.

FIG. 1 is an exploded view schematically illustrating the structure of the electrochemical test strip according to an embodiment of the invention. In FIG. 1, an electrochemical test strip 100 includes an insulating substrate 110, an electrode system 115, a lower separated plate 120, a reaction layer 130 and an upper separated plate 140. In one embodiment, the insulating substrate 102 can be an electrically insulating substrate, and its material may include, but are not limited to: polyvinyl chloride (PVC), glass fiber (FR-4), polyester suphone, bakelite, polyethylene terephthalate (PET), poly carbonate esters (PC), polypropylene (PP), polyethylene (PE), polystyrene (PS), glass plate, ceramic or any combination thereof.

Materials of the electrode system 115 can include any conductive material, such as palladium paste, platinum paste, gold paste, titanium paste, carbon paste, silver paste, copper paste, gold-silver mixed paste, carbon-silver mixed paste, or any combination thereof. In one embodiment, the electrode system 115 is composed of a carbon powder conductive layer. In another embodiment, the electrode system 115 is composed of a metal layer. In further another embodiment, the electrode system 115 is composed of a silver-based conductive layer and a carbon powder conductive layer located thereon, wherein impedance of the carbon powder conductive layer is typically much greater than those of the silver-based conductive layer or other metal layer.

According to some embodiments of the invention, in response to the actual measurement needs, the electrode system comprises an electrode set arbitrarily composed by a plurality of electrodes insulated from each other. The electrode set may include a plurality of electrodes insulated from each other. In one embodiment of the invention, the electrode system includes a first electrode set and a second electrode set. The first electrode set includes a first working electrode and a first reference electrode insulated from each other. The second electrode set includes a second working electrode and a second reference electrode. It should be noted that the working electrode and the reference electrode of the present invention are not limited to the conventional DC measurement system in which the working electrode is connected to the working side of the specie and the reference electrode is connected to the negative side of the working electrode. It can also be applicable to the first and second electrodes of the AC measurement system.

Note that the electrode configuration is not limited, as long as the electrodes form an electrical loop with the measuring instrument. In general, as long as each electrode of the electrode set is configured to act as the above-described function and the electrodes are insulated from each other prior to connection with the blood sample, it is sufficient to implement embodiments of the invention. Embodiments of the invention are not limited to arrangement relationship between the electrodes, nor be limited to the number of electrodes. It would be applicable to increase other electrodes depending on requirements of the application. The invention does not intend to limit the application of electrode system of the electrochemical test strip. The arrangement of the electrode system of the electrochemical test strip is described and illustrated as a schematic example of an embodiment of the invention. However, a person skilled in the art can easily replace or modify the use of electrode disclosed in the specification. For example, the electrode sets of the invention can be replaced with an electrode set for biochemical or other electrical detection purposes.

The lower separated plate 130 is disposed overlying the insulating layer 110, and the lower separated plate 130 includes a reaction region 125 and a port for sampling 122 exposing a portion of the electrode system. Generally, it would be sufficient to implement as long as the reaction region 125 exposes part of the electrode system. The present invention does not intend to limit the shape of the reaction region. Further, the connecting region 112 of the insulating substrate is exposed by the lower separated plate 120 such that one end of the connection area of the electrode system electrically connects the measuring instrument. Materials of the lower separated plate can include, but are not limited to a PVC insulating tape, a PET insulation tape, a thermal drying insulating paint or an UV curable insulating paint. Furthermore, during the manufacturing process of the lower separated plate, the lower separated plate with the trimmed opening can be placed on the insulating substrate and the electrode system. Alternatively, the lower spacer can be formed on part of the insulating substrate and the electrode system by directly printing and selectively avoid the reaction region.

The reactive layer 130 is located in the reaction region. The reactive layer at least covers a corresponding portion of the working electrode and the reference electrode in the reaction region, as long as it does not block the sampling port, to implement an electrochemical reaction or to generate a specific identification biological signal. The reactive layer may include at least one active material and conductive medium to generate a chemical reaction with the liquid sample (e.g., blood sample). In general, the area of the reactive layer is smaller than the area of the reaction region, and as long as the reaction layer undergoes a chemical reaction with the liquid sample, the shape of the reactive layer does not intend to be limited. In one embodiment, the active substance includes enzymes either being immobilized or immobilized, such as glucose diversified enzymes, antigens, antibodies, microbial cells, plant and animal cells, plant and animal tissues having components capable of identifying biological characteristics. Conductive media is configured to receive electrons generated after the reaction of the activating substance with the sample and to transfer the electrons to the biographical measuring instrument via the electrode unit. The composition of the reactive layer can be, but is not limited to enzyme (e.g., glucose glucoamylase), a conductive medium (e.g., potassium ferricyanide), a phosphate buffer, and a protecting agent (such as: protein, dextrin, dextran, amino acids, etc.).

Materials of the upper separated plate 140 can include, but are not limited to transparent or translucent material so as to easily observe whether the reaction zone is filled with the blood sample and to avoid testing under blood sample unfilled, resulting in erroneous measurements. The lower surface of the upper separated plate 140 near the reaction zone can be coated with a hydrophilic spacer (no shown) to enhance capillary action on the internal walls of the reaction zone and more rapidly and efficiently introduce the blood sample into the reaction zone. The upper separated plate 140 further comprises a vent hole 145 corresponding to the openings (not shown) to enhance capillary action, exhausting gas in the reaction zone. In general, the vent hole is disposed near the end of the inner closed opening. Embodiments of the present invention are not limited to the shape of the vent hole, for example, circular, oval, rectangular, diamond, etc.

In one embodiment, the electrochemical test strip 100 can be provided with an identification unit 150, which is formed on the side of upper surface of the electrode system which is in contact with the measuring instrument. The identification unit 150 includes a plurality of electrical components. The electrical component can be a variety of electrically conductive elements such as electrical elements having electrical characteristics of passive components. In one embodiment, the electrical element can be a resistor which is the same as the material of the electrode system. The electrical element can be formed by screen printing, imprinting, thermal transfer printing, spin coating, ink jet printing, laser ablation, deposition, electroplating, or screen-printing. In another embodiment, the electrical device comprised in the identification unit 150 may include resistors, capacitors, inductors, and/or combinations thereof.

When the identification unit is inserted in a measurement device, the measurement device can identify the location and quantity of each electrical component on the electrochemical test strip meter, thereby identifying the kind of the electrochemical test strip 100 and further adopting corresponding correction parameters or measurement modes. In other words, the number and location of a plurality of electrical components determine an identification code of the electrochemical test strip so that the measuring instrument can accordingly identify electrochemical test strip 100. The present invention does not intend to limit the number, shape and configuration of the electrical elements comprised in the identification unit. The present invention does not intend to limit the location and operating mode of identification unit. The only implement criteria for the identification unit is that the identification code can be read by the measuring instrument.

Figure 2A:
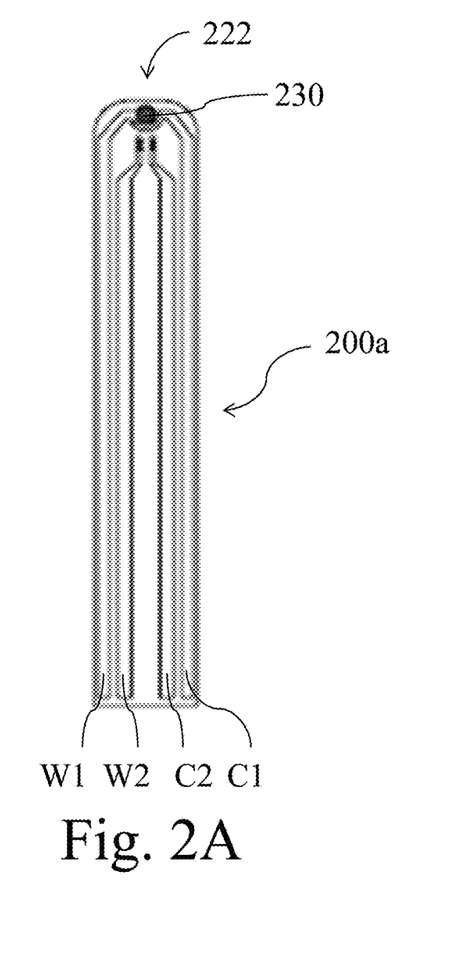
FIGS. 2A-2C schematically show layouts of the electrode system according to some embodiments of the present invention.
Figure 2B:
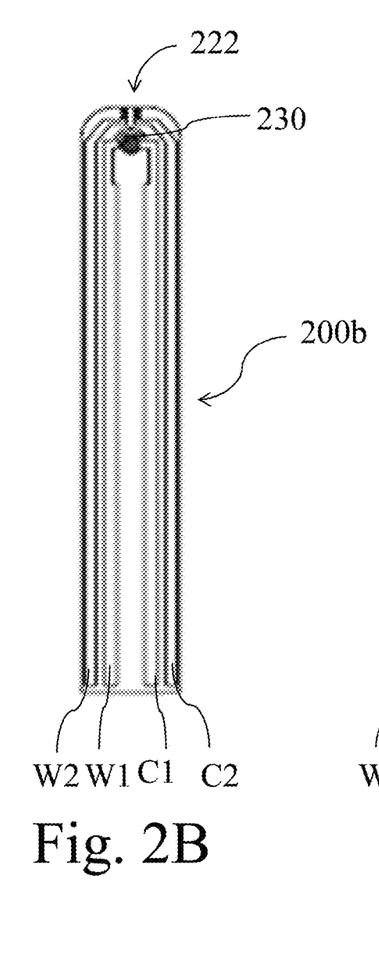
Figure 2C:
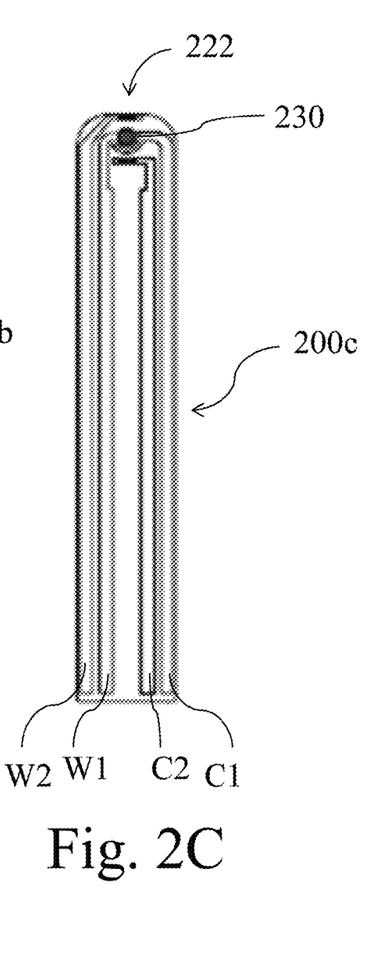

FIGS. 2A-2C schematically show layouts of the electrode system according to some embodiments of the present invention. Referring to FIGS. 2A-2C respectively, fulfilling the measurement requirements, an electrode system comprised a plurality sets of electrodes is disposed on a single electrochemical test strip. According to embodiments of the present invention, the electrode systems 200a-200c include but are not limited to a first set of electrodes and a second set of electrodes. The first set of electrodes which include at least one first working electrode W1 and first reference electrode C1 are configured to detect reaction signal of the sample with the reactive layer 230. The second set of electrodes which include at least one second working electrode W2 and second reference electrode C2 are configured to detect reaction signal of the sample without the reactive layer. In one embodiment, arrangement of the electrode sets of the electrochemical test strip is illustrated in FIG. 2A, the first working electrode W1 and the first reference electrode C1 of the first electrode set are disposed adjacent to the sampling port compared to the second electrode set. In another embodiment, arrangement of the electrode sets of the electrochemical test strip is illustrated in FIG. 2B, a second working electrode W2 and the second reference electrode C2 of the second electrode set are disposed adjacent to the sampling port compared to the first electrode set. In further another embodiment, arrangement of the electrode sets of the electrochemical test strip is illustrated in FIG. 2C, the first working electrode W1 and the first reference electrode C1 of the first electrode set are disposed between the second working electrode W2 and the second reference electrode C2 of the second electrode set. However, the present invention does not intend to limit the measurement manners of the first and the second electrode sets. In one embodiment, one electrode set detects a signal generated from the sample and the reaction layer, the other electrode set detects no signal from the reactive layer. In another embodiment, both electrode sets detect signals generated from the sample and the reaction layer. In further another embodiment, both electrode sets detect no signal from the reactive layer. Furthermore, in addition to the first and second electrode sets, there are other electrode set arrangements of the electrode system in the electrochemical test strip of the present invention. Note that the present invention does not intend to limit the measurement relationship and arrangement between the respective electrode sets, it is also applicable to adjust or modify electrical connection relationship based on the actual measurement needs. Each of the electrode sets can individually proceed with an individual measurements respectively, or one or more measurements can be performed on the same electrode set, such as disruptor and concentration measurements can be operated on the same electrode set. Another embodiment of the electrode system may include a ⊓ shape electrode, which is electrically insulated from each measurement electrode. The ⊓ shape electrode is configured to electrically connect with the measuring instrument. When the electrochemical test strip is inserted into the measuring instrument, an electrical loop is formed between the ⊓ shape electrode and the measuring instrument, thereby starting the measurement operation. Other embodiments of electrode arrangements and measurement methods are also disclosed in Taiwanese Patent Application No. 102142018, assigned to the same applicant and the entity of which is incorporated herein by reference.

Note that the present invention does not intend to limit the sequence of contacting the electrodes when the sample enters the reaction region. The position of the electrode sets can be adjusted based on actual measurement needs according to some embodiments of the present invention, as long as the electrode sets can sufficiently form a loop with the sample and complete implementation of the measurement. When the user manually or automatically inserts the test strip and starts the measuring instrument, the processor of the measuring instrument proceeds with detection through the electrode loop adjacent to the sampling port of the electrochemical test strip. The electrode loop adjacent to the sampling port is provided with the closest set of electrode loop to the sampling port of the electrochemical test strip. In FIG. 2A, for example, the electrode loop adjacent to the sampling port is assigned to the first electrode group, and in FIG. 2B, the electrode loop adjacent to the sampling port is assigned to the first electrode group. However, the present invention does not intend to limit the electrode loop adjacent to the sampling port to being required at the time of measurement. The original electrode loop can be altered due to the demand of an instrument hardware or software to achieve the effect of the electrode loop adjacent to the above-mentioned sampling port. Referring to FIG. 2C, the effect of the electrode loop adjacent to the sampling port can be achieved by changing the electrical connection relationship between the electrodes such that the second working electrode W2 are incorporated with the reference electrode C1.

Figure 3:
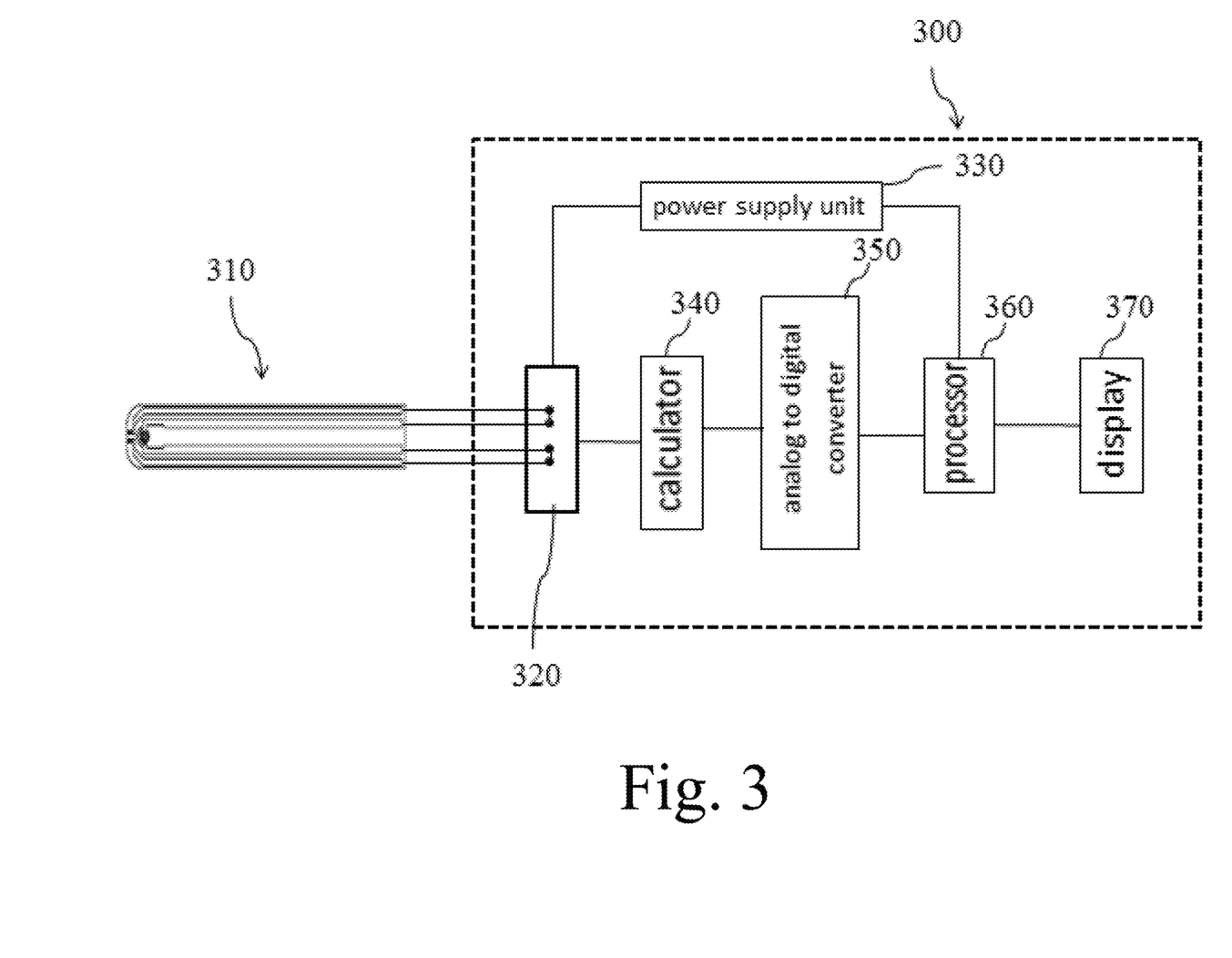
FIG. 3 shows a block diagram illustrating a connection relationship between an electrode unit of the electrochemical test strip in FIG. 1 and a measuring instrument.

FIG. 3 shows a block diagram illustrating a connection relationship between an electrode unit of the electrochemical test strip in FIG. 1 and a measuring instrument. Referring to FIG. 1 and FIG. 3, an exposed portion of the electrode system far away from an end of the reaction region is used for electrically connecting the measuring instrument and forming an electrical loop with the measuring instrument. In one embodiment, the measuring instrument 300 includes a connector 320 for external connection, a calculation unit 340 for converting concentration, an analog-to-digital converter (ADC) 350, a processor 360, a display unit 370 and a power supply 330. When the sample enters the reaction region of the electrochemical test strip 310, the sample will cover a portion of the electrode system. When the power supply 330 of the measuring instrument 300 applies an electrical signal to the electrode system, a response signal generated from the sample corresponding to the electrical signal is transmitted the calculation unit 340 of the measuring instrument 300 through the connector 320. Subsequently, the response signal is calculated by the calculation unit 340 converting it by the analog-to-digital converter 350 to obtain a digitized response signal. This digitized response signal is further processed by the processor 360 and/or is converted to a measurement result displayed on the display 370.

For simplification of the specification, the following description is only focused on the sample volume measurement. Those skilled in the art, however, can easily combine the sample volume measurements disclosed in the invention with other measurements of physiological parameters. For example, the volume of the blood sample can be acquired through the sample volume measurement method of the present invention, thereby using the sample volume value to calculate the biochemical concentration values, which are not limited to glucose, cholesterol, uric acid, lactic acid, and hemoglobin.

Figures 4A, 4B:
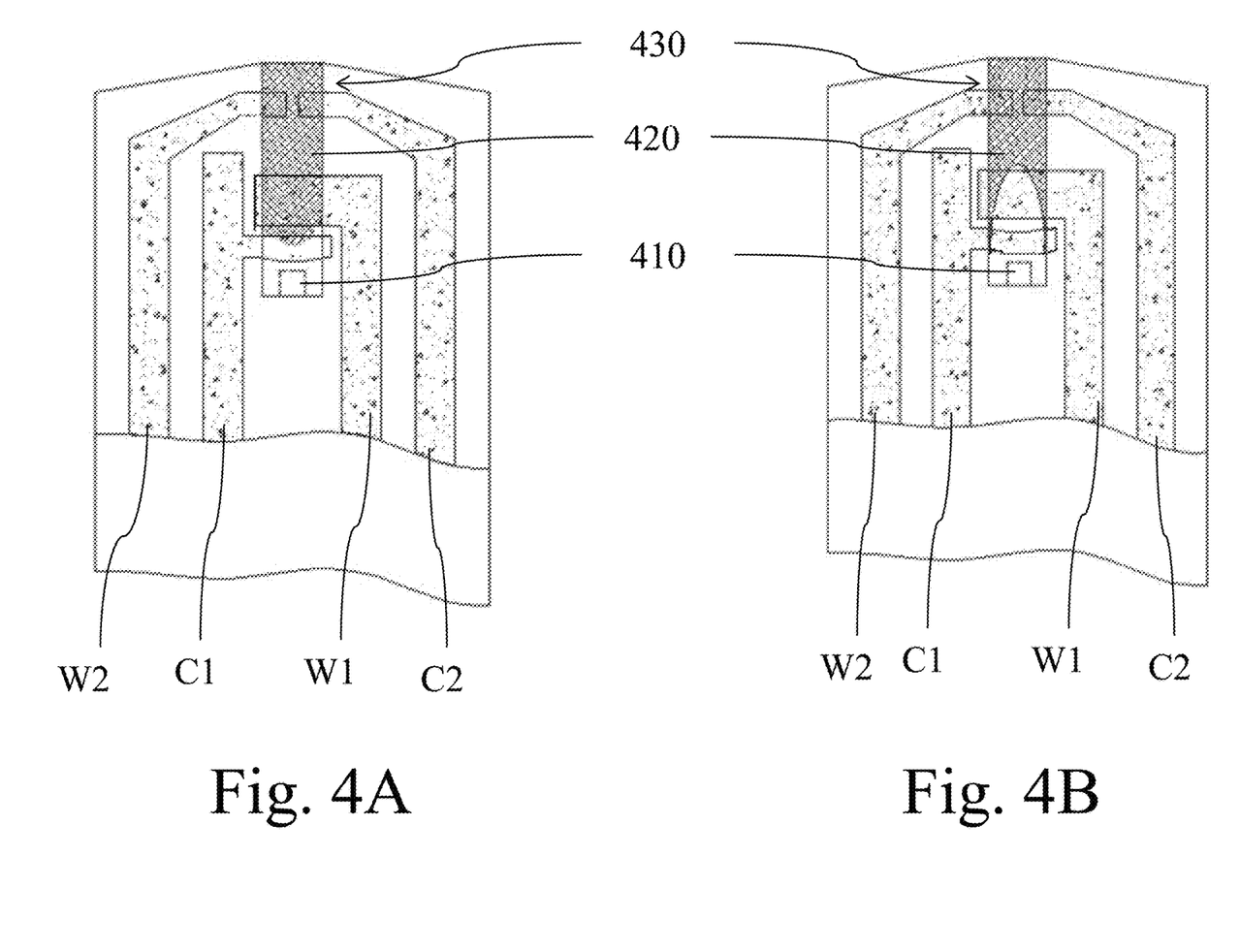
FIGS. 4A-4F are schematic diagrams illustrating each embodiment when insufficient sample covers each set of electrodes.
Figure 4C:
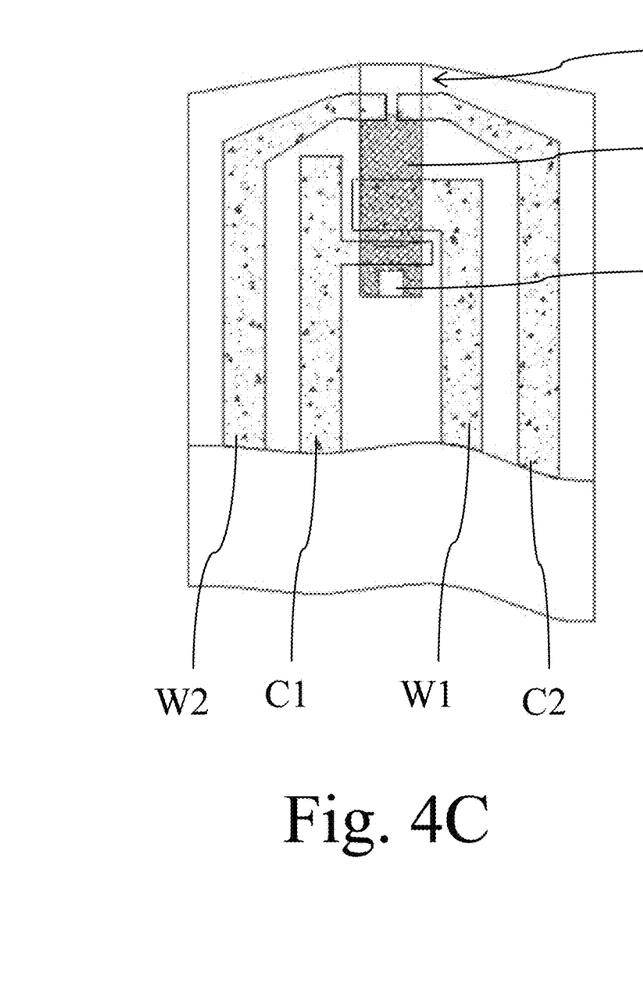
Figure 4D:
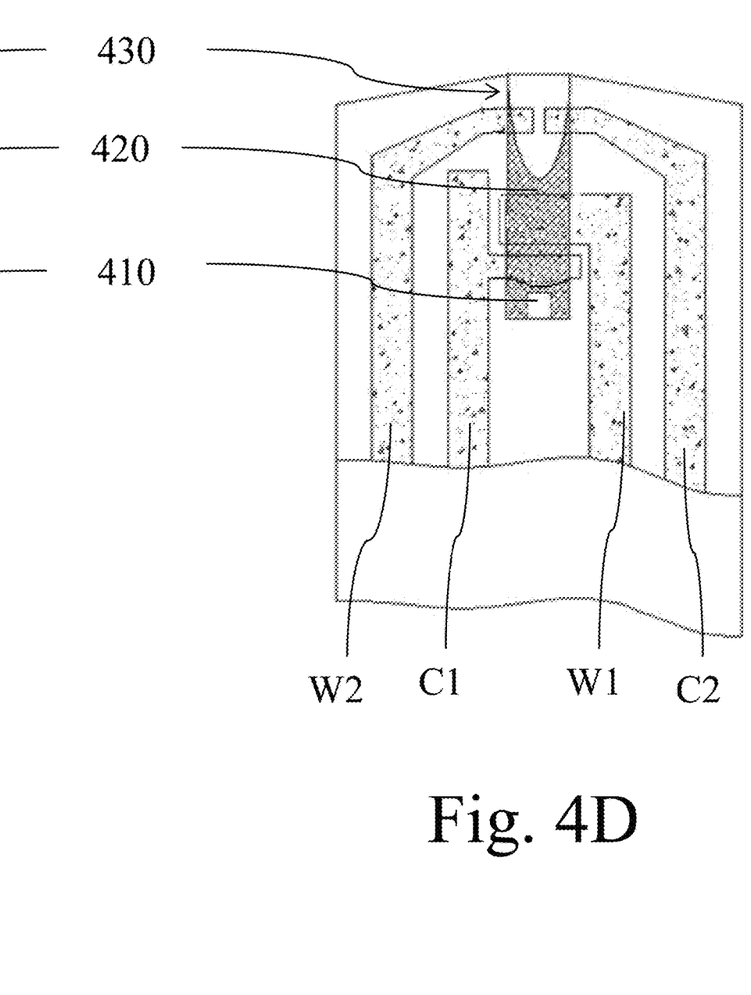
Figure 4E:
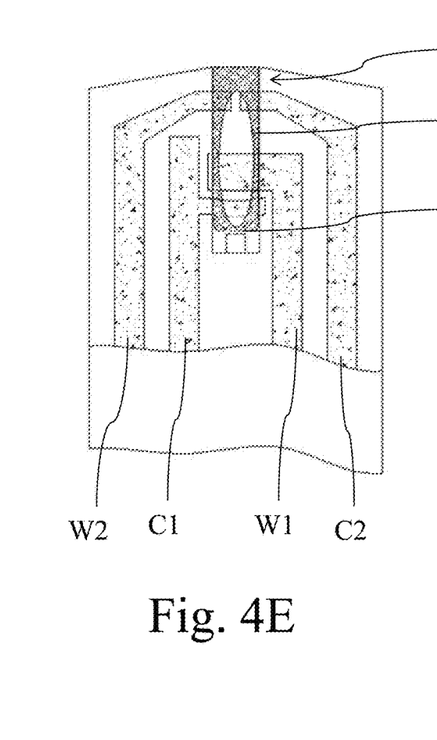
Figure 4F:
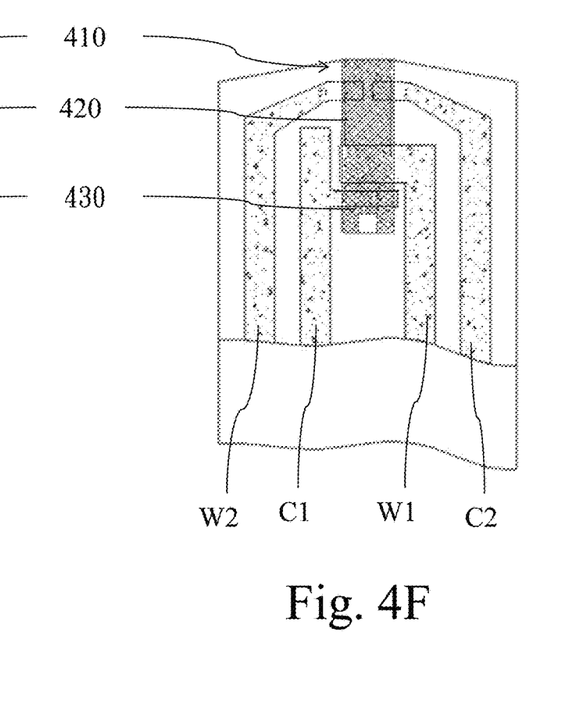

FIGS. 4A-4F are schematic diagrams illustrating each embodiment when insufficient sample covers each set of electrodes. Referring to FIGS. 4A and 4B, sample 420 covers the second set of electrodes and the first working electrode W1 in the reaction region 430, but merely in contact with a portion of the first reference electrode C1. The first working electrode W1 and the first reference electrode C1 are partially electrically conducted such that the signal on the first set of electrodes measured by the measuring instrument is weak with high resistance. In FIGS. 4C and 4D, the sample covers part of the second working electrode W2 and part of the second reference electrode C2, resulting in partially electrical conduction between the second working electrode W2 and the second reference electrode C2. The signal on the second set of electrodes measured by the measuring instrument is weak with high resistance. Further in FIG. 4E, even though the sample covers each of the electrodes, but it is still blank in the center, resulting in the signal on the first and second sets of electrodes still weak with high resistance. Further, the predetermined response signal in the measuring instrument is defined by the chemical response signal generated when the reactive layer on the reaction region is completely filled and the in each set of electrodes is covered with the sample as shown in FIG. 4F. When the sample volume in the reaction region is under expected, i.e., insufficient sample capacity, resulting in incomplete reaction of the reactive layer on the measuring electrode, severely undervalued data by measurements, and erroneous measurements. For example, while proceeding with blood glucose measurement, if the blood sample content in reaction region of the electrochemical test strip is too low, weaker electrical signal will be obtained by the measuring instrument than the predetermined value, misleading the calculation unit from a high blood glucose level to a low blood glucose level.

Figure 5:
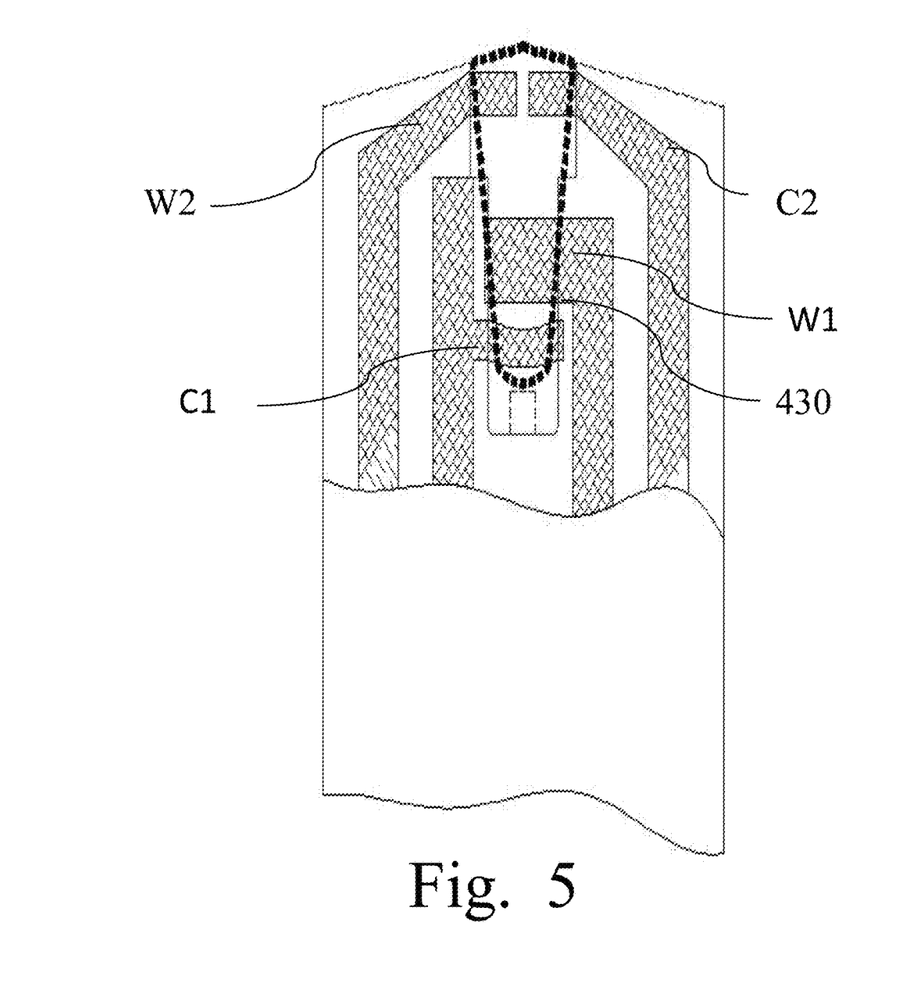
FIG. 5 is a partial perspective view schematically illustrating an electrochemical test strip according to an embodiment of the present invention.

FIG. 5 is a partial perspective view schematically illustrating an electrochemical test strip according to an embodiment of the present invention. According to an embodiment of the present invention, the second set of electrodes is implemented as an electrode loop adjacent to the sampling port. When the measuring instrument detects injection of the samples into the reaction region 430 of the electrochemical test strip, a signal is applied to the first and the second sets of electrodes. If the sample covers one set of electrodes and creates an electrical loop, the measuring instrument can determine whether the sample has already covered the set of electrodes. The first and the second sets of electrodes in the electrochemical test strip are respectively disposed at the front and rear ends of the reaction region from the sample port. When the first working electrode W1 and the first reference electrode C1 of the first set of electrodes and the second working of and electrode W2 and the second reference electrode C2 of the second set of electrodes are all electrically conducting, whether the sample has been completely covered the entire reaction regions can be determined. The present invention does not intend to limit the sequence of applying signals. In some embodiments, the signals can be applied to the first and the second sets of electrodes at the same time. Alternatively, after the signal is applied to the second working electrode W2 and the second reference electrode C2 of the second set of electrodes, the signal is then applied to the first working electrode W1 and the first reference electrode C1 of the first set of electrodes. It can also be applicable of using a timer dividing electrical signals to the first and the second sets of electrodes.

According to another embodiment of the present invention, it is also applicable of using the second set of electrodes as the electrode loop adjacent to the sampling port. When the measuring instrument determines the sample entered the reaction region of the electrochemical test strip, a sample potential difference exists due to the external energy from the measuring instrument applied to the reaction region. Therefore, a diffusion signal is generated by the effect of diffusion. Calculating the volume signal through the diffusion current can thus become possible. The diffusion current calculation method satisfies the following equation:

$$I = \frac{nFAC\sqrt{D}}{\sqrt{\pi t}}$$

where I denotes reaction current, n denotes electron transfer number, F denotes Faraday constant, A denotes an area of the working electrode, t denotes time and D denotes diffusion constant.

A signal is applied to the first and the second sets of electrodes such that the first set of electrodes generates a first volume signal and the second set of electrodes generates a second volume signal. Since the first set pf electrodes is provided with a reaction layer which undergoes chemical reaction with the sample and generates electrical signals, but the second set of electrodes does not comprise such a reactive layer, when the sample volume is sufficient the first volume signal is higher than the second volume signal. High signal can be obtained by calculating the signal difference generated from the reactive layer and the sample at a specific time interval by using electrochemical diffusion current. Therefore, the first and the second signal volume signals deviated within a reasonable range can be calculated using the diffusion current measurement method.

TABLE I determination chart of sample volume signals

| Sample Status | First Volume Signal | Second Volume Signal | Determination by the Measuring Instrument |
|---|---|---|---|
| FIG. 4A | weak | strong | sample deficiency |
| FIG. 4B | weak | strong | sample deficiency |
| FIG. 4C | strong, exceeding reasonable range | weak | sample deficiency |
| FIG. 4D | strong, exceeding reasonable range | weak | sample deficiency |
| FIG. 4E | equal to the second volume signal | equal to the first volume signal | sample deficiency |
| FIG. 4F | strong, with reasonable range | weak | proceeding with concentration measurement |

Referring to FIG. 1, when the first volume signal is higher than the second volume signal, but is still within a reasonable range, the measurement instrument determines that the amount of sample is sufficient (also shown in FIG. 4F) and proceeds with the concentration detection procedures. When the first volume signal is higher than the second volume signal, the measurement instrument determines that the sample does not completely cover the first set of electrodes as shown in FIG. 4A or FIG. 4B. When the second volume signal is higher than the first volume signal and exceeds the reasonable range, the measurement instrument determines that the sample does not completely cover the second set of electrodes as shown in FIG. 4C or FIG. 4D. When the first volume signal is equal to the second volume signal, the signal is weak but does not affect the reasonable determination due to just a minor reaction occurred between the sample and the reactive layer on the first set of electrodes. The measuring instrument can still effectively determine that the sample does completely covers the first and the second sets of electrodes (as shown in FIG. 4E). The volume of the reaction region can be determined by the difference between the first and the second volume signals. By alerting the user inadequate sample volume of showing warning sign on a display, repeating the measurement procedures or adding more sample to the reaction region are requested.

Note that the present invention does not intend to limit the relationship between the reactive layer and the sets of electrodes. It is adjustable base on the needs for measurement and the diffusion current calculation method. In one embodiment, the first set of electrodes is covered with a first reactive layer, and the second set of electrodes is covered with a second reactive layer. The diffusion currents on the first and the second reactive layers can be respectively calculated using the diffusion current calculation method and a reasonable range is then acquired to determine the sample volume in the reaction region. In another embodiment, the first and the second sets of electrodes do not applied with reactive layers. Since diffusion motion still occurs in the sample, the reasonable range can be easily defined to determine the sample volume in the reaction region.

Further, the present invention does not intend to limit the connection relationship of the electrical loop between the first and the second sets of electrodes. The connection relationship of the electrical loop between the sets of electrodes can also be reached using a measuring instrumental hardware or software to alter the original electrical loop. According to a further embodiment of the present invention, the electrical connection relationship between the electrodes can be changed using the measurement instrument. For example, the second working electrode W2 incorporated with a first reference electrode C1 consist of an electrical loop in the first set of electrodes as shown in FIG. 5. The first working electrode W1 incorporated with a second reference electrode C2 consist of an electrical loop in the second set of electrodes. By crossly referencing the first volume signal with the second volume signal, the sample volume in the reaction region can be more precisely determined. In another embodiment, the measuring instrument presets a reasonable range when the first and the second sets of electrodes respectively detect a volume signal which is then compared with the preset reasonable range. If the volume signal is consistent with a reasonable signal range, then a sufficient volume is determined, and the measuring instrument may further proceed with the concentration detection procedures. On the contrary, if the volume signal does not match the preset reasonable range, the measuring instrument determines deficiency of the sample volume in the reaction region. By alerting the user inadequate sample volume of showing warning sign on a display, repeating the measurement procedures or adding more sample to the reaction region are requested.

Note that the present invention does not intent to limit the patterns of the volume signals, as long as the determination can be made by the measuring instrument. The patterns of the volume signal can be, but is not limited to the resistance value, capacitance value, reactance value, current value, voltage value, the reaction phase angle, slope and/or any combination thereof. In general, any electrical signal having significance is sufficient to implement.

Figure 6:
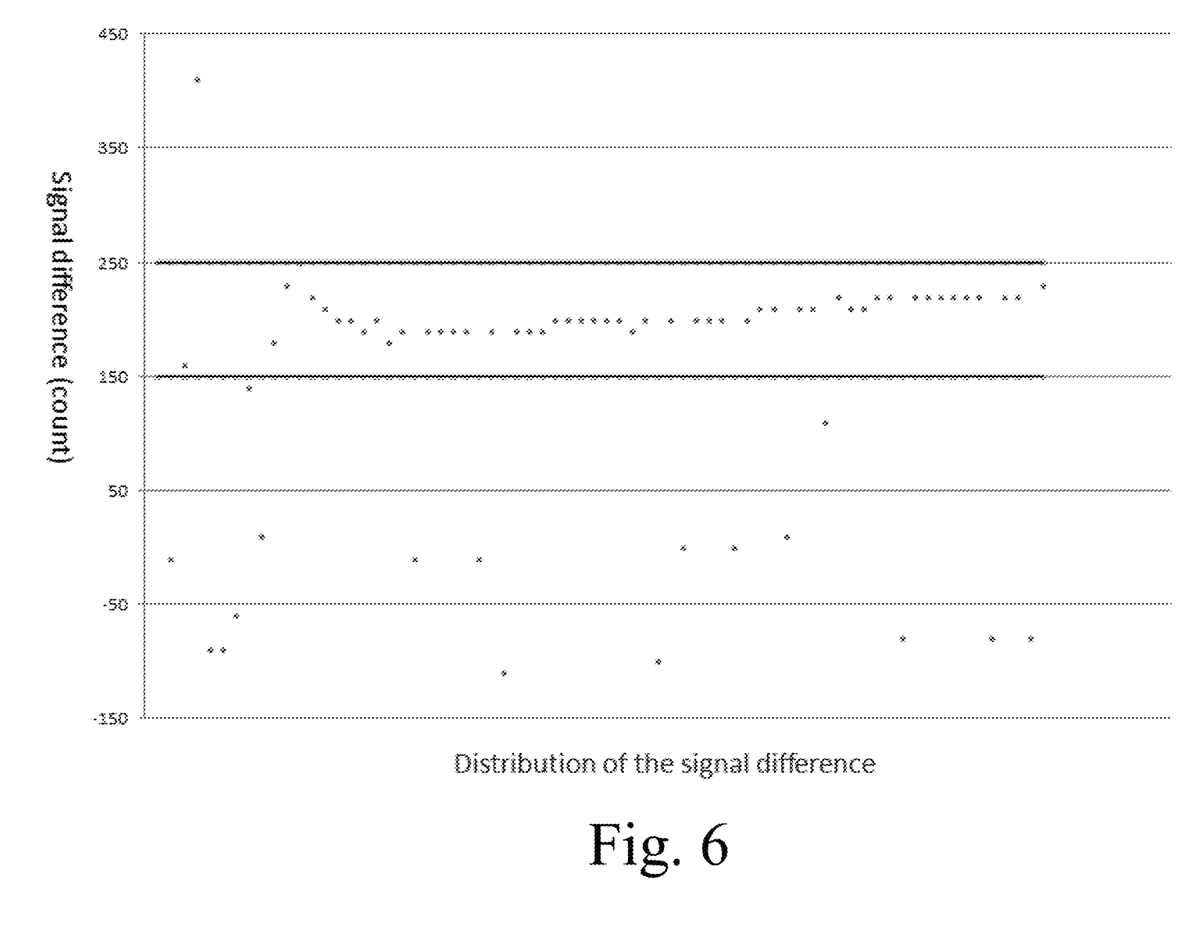
FIG. 6 shows the distribution of the measured signals implemented by the determination method according to embodiments of the present invention.

In order to further confirm the effect of utilizing the difference between the first and the second volume signals to determine the sample volume in the reaction region, FIG. 6 shows the distribution of the measured signals implemented by the determination method according to embodiments of the present invention. In one embodiment, the signal difference within the reasonable range is about in a range between 150-250 counts. The measuring instrument determines that the electrochemical test strip which the difference between the first and the second volume signals falls within this range has a sufficient amount of sample volume. The measuring instrument can proceed with the concentration measurement. On the contrary, those electrochemical test strips having signal difference not within the reasonable range do not have sufficient amount of the sample volume. Adding more samples to the reaction region has to be requested. Thus, the measuring instrument can easily determine the sample volume in the reaction region using the difference between the first and the second volume signals.

Figure 7:
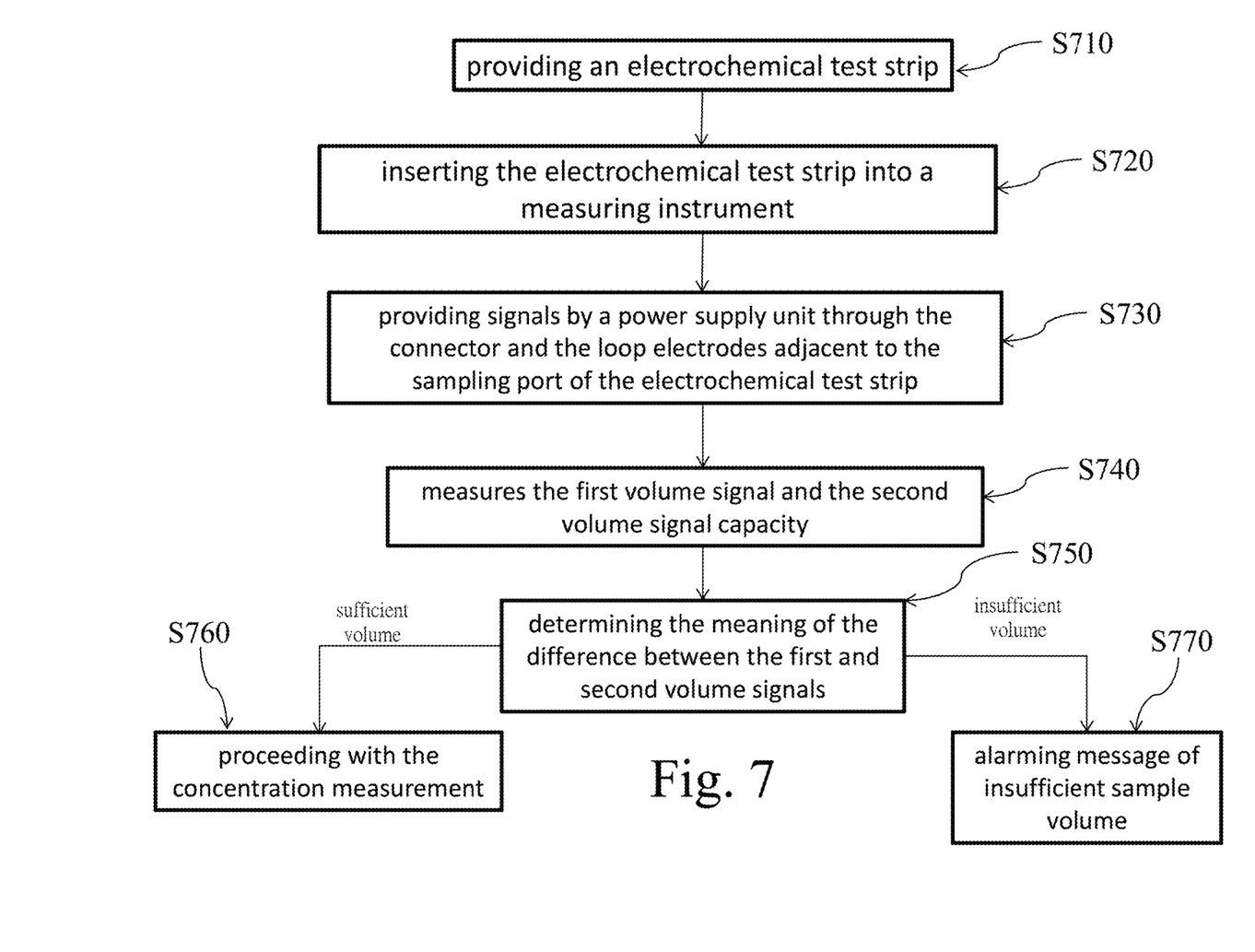
FIG. 7 is a flow chart illustrating a method for determining the sample volume in reaction region using difference between the first and second volume signals according to embodiment of the present invention.

FIG. 7 is a flow chart illustrating a method for determining the sample volume in reaction region using difference between the first and second volume signals according to embodiment of the present invention. First, an electrochemical test strip for measurement is provided (step S710). The electrochemical test strip may include, but is not limited to four electrodes insulated from each other: a first working electrode, a first reference electrode, a second working electrode and a second reference electrode. Next, the electrochemical test strip is inserted into a measuring instrument (step S720). The measuring instrument can be started by the insert action or be started manually. After starting the measuring instrument, a signal is provided by the power supply unit through the connector and the loop electrodes adjacent to the sampling port of the electrochemical test strip (step S730). Subsequently, when the measuring instrument detects the sample into the reaction region, it measures the first volume signal and the second volume signal capacity and calculates the difference between the first and second volume signals (step S740). Thereafter, the difference between the first and second volume signals is analyzed by the signal processor (step S750). If the sample volume is sufficient, then the concentration measurement procedures can proceed (step S760). If the sample volume is insufficient, repeating measurement or adding more samples to the reaction region has to be requested (step S770).

While the invention has been described by way of examples and in terms of preferred embodiments, it would be apparent to those skilled in the art to make various equivalent replacements, amendments and modifications in view of specification of the invention. Therefore, the scope of the appended claims should be accorded the broadest interpretation so as to encompass all such replacements, amendments and modifications without departing from the spirit and scope of the invention.

The invention claimed is:

1. A method for determining a sample volume in a reaction region of an electrochemical test strip, comprising:
   providing the electrochemical test strip comprising:
     an insulator substrate with an electrode system disposed thereon, the electrode system comprising at least one first set of electrodes and second set of electrodes;
     a lower separated plate disposed on the insulator substrate and including a reactive region and a port for sampling;
     a reactive layer placed on the reaction region; and
     an upper separated plate disposed above the lower plate,
   wherein the first set of electrodes is designed for a first signal loop for sample volume and the second set of electrodes is designed for a second signal loop for sample volume characterized in that the first and second signal loops reflect on a volume of the reaction region;
   placing the electrochemical test strip into an electrochemical measurement system;
   providing an electrical test signal to the first and second sets of electrodes of the electrochemical test strip;
   performing measurement of a first volume signal and a second volume signal using the electrochemical measurement system; and
   analyzing and determining a sample volume in the reaction region based on a signal difference between the first and the second volume signals using a signal processor, if the sample volume is sufficient, then proceeding with a concentrating measurement step; if the sample volume is deficient, then demanding redo measurement or adding more sample to the reaction region,
   wherein calculation of the signal difference between the first and the second volume signals is based on a diffusion current calculation method using a calculation unit; and
   wherein the diffusion current calculation method satisfies the following equation:

$$I = \frac{nFAC\sqrt{D}}{\sqrt{\pi t}}$$

where I denotes reaction current, n denotes electron transfer number, F denotes Faraday constant, A denotes an area of the working electrode, t denotes time and D denotes diffusion constant.

2. The method as claimed in claim 1, wherein the electrical test signal is applied to the first and second sets of electrodes at the same time.

3. The method as claimed in claim 1, further comprising using a timer dividing the electrical test signal to the first and second sets of electrodes.

\* \* \* \* \*